United States Patent [19]
Schulz et al.

[11] Patent Number: 5,705,664
[45] Date of Patent: Jan. 6, 1998

[54] MONONOBLE METAL DITHIOLATES, PREPARATIONS CONTAINING THEM AND THEIR USE

[75] Inventors: Andreas Schulz, Neu-Isenburg; Marco Höfler, Freigericht, both of Germany

[73] Assignee: Cerdec Aktiengesellschaft Keramische Farben, Frankfurt, Germany

[21] Appl. No.: 390,480

[22] Filed: Feb. 17, 1995

[30] Foreign Application Priority Data

Feb. 21, 1994 [DE] Germany .......................... 44 05 423.8
Feb. 24, 1994 [DE] Germany .......................... 44 05 933.7

[51] Int. Cl.$^6$ .................. C07F 1/08; B41M 3/12; B05D 3/00; B05D 5/00
[52] U.S. Cl. .................. 556/113; 101/129; 427/150; 427/195; 427/201; 427/271; 427/287; 556/116; 106/287.18
[58] Field of Search .................. 556/113, 116; 427/150, 195, 201, 271, 287; 101/129; 106/287.18

[56] References Cited

U.S. PATENT DOCUMENTS

| 5,162,556 | 11/1992 | Maeda et al. ............ 556/113 |
| 5,235,079 | 8/1993 | Lotze et al. ............ 556/113 |
| 5,252,764 | 10/1993 | Lotze et al. ............ 556/113 |

FOREIGN PATENT DOCUMENTS

| 650868 | 10/1962 | Canada . |
| 0 491 143 | 6/1992 | European Pat. Off. . |
| 0 491 147 A1 | 6/1992 | European Pat. Off. . |
| 0 514 073 | 11/1992 | European Pat. Off. . |
| 3 217 049 | 11/1982 | Germany . |
| 2 216 536 | 10/1989 | United Kingdom . |

OTHER PUBLICATIONS

Petrun'kin, Chemical Abstracts, No. 7 10 Apr., 1957 Abstract No. 5692h.
Isab et al., Journal of the Chemical Society, Chemical Communications No. 24, 15 Dec. 1976, Letchworth GB, pp. 1051–1052.
Elvers, Ullmann's Encyclopedia of Industrial Chemistry, 5th Edition, vol. A 24 pp. 81–85 (1993).

*Primary Examiner*—Porfirio Nazario-Gonzalez
*Attorney, Agent, or Firm*—Wenderoth, Lind & Ponack

[57] ABSTRACT

The invention relates to mononoble metal dithiolates, more particularly water-soluble monogold(I) dithiolates, to their production and to their use for the production of noblemetal-containing decorations on firing-resistant substrates.

The mononoble metal dithiolates represent a new class of water-soluble thiolates for use in organic-aqueous and essentially purely aqueous noble metal preparations for decoration purposes.

The mononoble metal dithiolates correspond to the following formula:

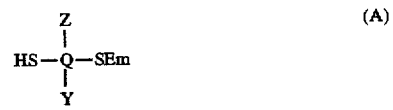

(A)

in which

Em=Au(I), Ag(I), an equivalent of Pd(II), Pt(II) or Rh(III),
Q=a tetravalent organic radical containing 2 to 10 carbon atoms,
Y=a hydrophilic group from the series comprising —COOH, —COO$^-$cat$^+$ or —COO—(CHR$^1$—CHR$^2$—O)$_m$R$^3$
Z=Y or H or a group from the series comprising —OR', —SR', —SO$_3$R', —NR'$_2$, —NR$_3$$^+$X$^-$.

28 Claims, No Drawings

MONONOBLE METAL DITHIOLATES, PREPARATIONS CONTAINING THEM AND THEIR USE

DESCRIPTION

This invention relates to mononoble metal dithiolates, more particularly water-soluble monogold(I) dithiolates, to their production and to their use for the production of decorations containing noble metals, more particularly high-gloss decorations of a coherent noble metal film, on firing-resistant substrates. The present invention also relates to noble-metal-containing preparations and transfers for decorating firing-resistant substrates which contain at least one mononoble metal dithiolate according to the invention.

So-called noble metal preparations, for example bright gold preparations and burnished gold preparations, have long been used for the production of a noble metal decoration, more particularly a decoration consisting essentially of gold and/or silver in the form of a high-gloss metal film, including conductors of—in particular—gold in integrated circuits, on a firing-resistant substrate. These noble metal preparations generally contain one or more organosulfur noble metal compounds, so-called noble metal thiolates, which are soluble in an organic carrier medium or in an organic/aqueous carrier medium, the noble metal being present in the monovalent oxidation stage in the case of Ag and Au. Besides the noble metal compound, the solvent and one or more organic polymeric binders, the preparations in question also contain one or more fluxes, such as for example so-called resinates and/or simple salts, oxides or coordination compounds of one or more of the elements boron, silicon, vanadium, chromium, indium, zinc, antimony, bismuth and rhodium, together with further auxiliary substances to adjust the processing and intrinsic properties. The noble metal preparations are applied to the surface to be coated by conventional direct or indirect printing processes, spraying or brushing or by the transfer technique. Evaporation of the solvent is followed by firing at a temperature adapted to the substrate and to the gold preparation; the maximum firing temperature is generally between 400° and 900° C., although even higher temperatures may be applied in special cases. A noble metal film is formed and fixed on the surface of the substrate by the firing operation. It is well known among experts that, to obtain high-gloss noble metal films, the noble metal thiolate used, the binder system and the solvent system have to be carefully coordinated with one another to produce bright decoration-forming films—including printed circuits for electrical/electronic purposes—firmly adhering to the substrate.

For some time, the organosulfur compounds used for the decorative preparations mentioned have been almost exclusively so-called gold sulforesinates obtained from a gold salt and sulfurized, more particularly naturally occurring terpenes. Synthetic noble metal thiolates, more particularly gold (I) thiolates corresponding to the general formula Au—S—R, where R is in particular an alkyl, cycloalkyl, aryl or aralkyl group or a bicyclic hydrocarbon radical, have recently been acquiring significance. The gold(I) thiolates mentioned generally required the use of an exclusively organic solvent system, cf. for example EP-B 0 491 143.

For industrial hygiene, safety and ecological reasons, there is increasing interest in noble metal preparations for decorating firing-resistant substrates in which the organic solvent of the solvent system is at least partly replaced by water. Thus, DE-OS 32 17 049 describes a paint for applying an overglaze decoration to porcelain which contains 15 to 40% by weight of polyvinyl pyrrolidone or a mixture of polyvinyl pyrrolidone and aqueous polyethylene oxide, 45 to 85% by weight of ethylene glycol and/or propylene glycol and optionally water. The document in question mentions oxides, gold and organic gold compounds as coloring constituents but does not disclose a single structure of the gold compounds.

A burnished gold preparation containing polyvinyl pyrrolidone and water and, in addition, an aqueous acrylate resin dispersion as binder and gold powder and/or a poorly soluble gold compound as coloring component is known from GB-A 2,216,536. It can be seen from the Examples that alcoholic solvents are also always present in these preparations. The preparations in the examples additionally contain a quantity of 5 or 6 wt. % of a non-ionic wetting agent. There is no indication in this document of using a water-soluble gold compound nor of dispensing with the presence of glycols and alcohols. As has been found in practice, noble metal preparations based on the documents cited above often lead to decorations which lack gloss.

EP-A 0 514 073 describes homogeneous compositions, preferably solutions, which form a bright metallic noble metal film on firing. These compositions contain 3 to 22% by weight of a noble metal thiolate, a polymeric resin and, as solvent system, a mixture of water and an organic solvent (co-solvent), preferably a water-miscible alcohol, ether or ester. Both the noble metal thiolate and the binder are said to be soluble in the water/co-solvent mixture. The gold(I) thiolates preferably used are those corresponding to the general formula Au—S—R—H or Au—S—R—X, where X is a nitro group or —COOH, —SO$_2$OH, AOH, —CONH$_2$, —NH$_2$ or —O—P(O) (OH)$_2$, the hydrogen atoms optionally being substituted, or salts thereof and R is a divalent organic radical. It is clearly apparent from numerous Examples and Comparison Examples in the cited document that only very special gold(I) thiolates in corresponding gold preparations lead to high-gloss decorations which adhere firmly to the decorated substrate. As can be seen from the Comparison Examples appearing in this document, it was only possible to obtain dull-looking decorations with some of the gold(I) thiolates corresponding to the above formulae, including for example gold(I) mercaptosuccinic acid.

Accordingly, the problem addressed by the present invention was to provide another group of noble metal thiolates which would be suitable for the production of high-gloss noble metal decorations on firing-resistant substrates. The new noble metal thiolates would develop their effect in particular in bright noble metal preparations containing an aqueous-organic and more particular a purely aqueous solvent system. Use of the new noble metal thiolates is intended to be applicable in a reliable way and to give rise to aesthetically high-quality, in particular high-gloss, pore- and spot-free decorations having good adhesion on stovable substrates.

It has surprisingly been found that the introduction of a second sulfhydryl group into the organic compound on which the noble metal thiolate is based considerably improves the suitability of the noble metal thiolate as a constituent of decorative noble metal preparations for the production of high-gloss decorations.

Accordingly, the present invention relates to mononoble metal dithiolates corresponding to general formula (A):

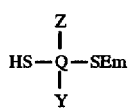

in which
- Em is a noble metal from the Au(I) or Ag(I) series or an equivalent of Pd(II), Pt(II) or Rh(III),
- Q is a tetravalent organic radical containing 2 to 10 carbon atoms,
- Y is a hydrophilic group from the series comprising —COOH, —COO⁻cat⁺, where cat⁺=Li⁺, Na⁺, K⁺, NH₄⁺, $(C_{1-3}alkyl)_n$ $N^+H_{(4-n)}$ or (hydroxy-$(C_{1-3})$-alkyl)$_n$ $N^+H_{(4-n)}$ and n is an integer of 1 to 4, or

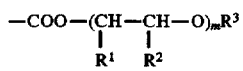

where $R^1$, $R^2$ and $R^3$ may be the same or different and represent H or methyl and m is an integer of 1 to 12, Z has the same meaning as Y or represents —H or a group from the series consisting of —OR', —SR', —SO₃R', —NR'₂, NR'₃⁺X⁻, where X⁻ is a mineral acid or carboxylic acid anion and R' is hydrogen or the group

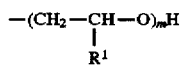

and $R^1$ and m are as defined above. Preferred mononoble metal dithiolates contain gold or silver, more particularly gold, as the noble metal.

The tetravalent organic radical Q and the substituents Z and Y are preferably selected in such a way that the resulting mononoble metal dithiolate shows high solubility in water. High solubility in water is obtained in particular when Y and/or Z represent(s) COO⁻cat⁺.

Where Y and/or Z represent(s) —COO⁻cat⁺ in the mononoble metal dithiolates according to the invention, the ammonium cations mentioned are preferred to the alkali metal cations. In the case of the alkyl ammonium cations, alkyl may represent methyl, ethyl, n-propyl or i-propyl. The alkyl ammonium cations may be mono-, di-, tri- or tetraalkyl ammonium with the above-mentioned alkyl groups, which may even be mixed. In the mono-, di-, tri- or tetra-hydroxyalkyl ammonium cations, the hydroxyalkyl group stands for hydroxymethyl, hydroxyethyl, 2-hydroxypropyl or 3-hydroxypropyl. Where Y and/or Z represent(s) carboxyl, the salts mentioned may readily be produced by a typical neutralization reaction using the corresponding amine or ammonium hydroxide.

Where Y represents the group —COO(CHR¹—CHR²—O)$_m$R³, m is preferably an integer of 3 to 7. Mononoble metal dithiolates in which Z is hydrogen naturally show lower solubility in water and hence are less suitable for water-containing noble metal preparations than compounds in which Z itself is a hydrophilic group.

The organic radical Q contains between 2 and 10 carbon atoms. The radical may additionally contain oxygen, nitrogen or sulfur atoms, for example in the form of hydroxyl, carboxyl, alkoxy, amino, alkylamino, mercapto or alkyl mercapto groups. In a particularly preferred embodiment, the organic radical Q is a $C_2$, $C_3$ or $C_4$ alkane tetrayl radical. In another embodiment, the organic radical Q is a 5-membered or 6-membered cycloaliphatic tetrayl radical, one ring C atom being replaceable by oxygen (—O—) or an imino group (—NH— or —NR—). Accordingly, the cyclic radicals Q are cyclohexanetetrayl, cyclopentanetetrayl, tetrahydrofurantetrayl, pyrrolidinetetrayl, piperidinetetrayl or tetrahydropyrantetrayl.

In the mononoble metal dithiolates according to the invention, the SH group and SEm group may be attached at adjacent carbon atoms or at carbon atoms separated from one another by one or more members. Compounds in which the SH and SEm group are positioned at adjacent carbon atoms are particularly preferred. Accordingly, mononoble metal dithiolates, more particularly monogold(I) and monosilver dithiolates of dimercaptosuccinic acid, 2,3- or 2,4-dimercaptoglutaric and 2,3- or 3,4- or 2,5-dimercaptoadipic acid and salts thereof with the cation cat⁺, are particularly preferred. As already mentioned, it is particularly useful to form a salt of the mononoble metal dimercaptosuccinic acid with a mono-, di- or tri-$(C_{1-3})$-alkylamine or mono-, di- or tri-(hydroxy-$(C_{1-3})$-alkyl)-amine. An amine from the group consisting of mono-, di- or triethanolamine and triethyl-, tri-n- or tri-iso-propylamine in a quantity sufficient to neutralize the carboxyl groups present are particularly suitable for salt formation. Said amines are also suited for forming salts with other inventive mononoble metal dithiolates.

Mononoble metal dithiolates having the structure described above have never been described before and, accordingly, have never been proposed for use for the production of metallic noble-metal-containing decorations on firing-resistant substrates. On the basis of the property comparison of decorations produced on the one hand with mononoble metal dithiolates according to the invention and on the other hand with known structurally similar noble metal thiolates in which there is no additional SH group, it is assumed that the mononoble metal thiolates according to the invention are stabilized by the additional SH group to such an extent that a coherent, firmly adhering, high-gloss noble metal film can be formed during the firing of the noble metal compound applied to a firing-resistant substrate, such as glass, porcelain and ceramic.

The mononoble metal dithiolates corresponding to general formula (A'):

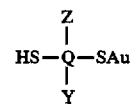

in which Q, Y and Z are as defined above, are produced in basically the same way as known noble metal thiolates, cf. the documents cited at the beginning. In the case of the monogold(I) dithiolates, a gold(I) complex corresponding to the formula AuCl-(R"SR'") is formed from tetrachloroauric acid after addition of twice the equivalent quantity of a thioether R"S'". The complex thus formed is then reacted with a substantially equivalent molar quantity of a dithiol (dimercapto compound) corresponding to general formula (B):

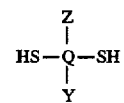

in which Q, Y and Z are as defined for formula (A'), in the presence of a solvent. A particularly suitable thioether for the formation of the gold(I) complex is methionine.

The production of the dithiol compound (B) comprises typical process steps. For example, dimercaptoalkane dicarboxylic acids can be obtained by reacting the corresponding alkine dicarboxylic acids with thioacetic acid. Another possible method of obtaining aliphatic and cyclic dimercapto compounds corresponding to general formula (B) is to react the corresponding dihalogen compound (Z—Q(Hal)$_2$—Y) with an alkali metal sulfide. Ag compounds according to the invention may readily be obtained by reacting a soluble Ag salt with a dithiol (B). Pd and Pt compounds according to the invention can be similarly obtained from a Pd(II) or Pt(II) salt and the dithiol, in this case in a molar ratio of around 1:2.

The mononoble dithiolates according to the invention may be used with advantage in the form of noble-metal-containing preparations for decorating firing-resistant substrates, more particularly glass, porcelain and ceramic. The preparations in question contain at least one mononoble metal dithiolate according to the invention, one or more polymeric organic binders and, typically, solvents, preferably an aqueous/organic or especially preferred an essentially purely aqueous solvent system, to dissolve the organic polymers and the mononoble metal dithiolate or otherwise to guarantee uniform distribution. If necessary, the noble-metal-containing preparations additionally contain auxiliaries to obtain the required processing properties, for example a screen-printable viscosity and a high drying rate of the preparation, and to establish certain optical properties—color tones—and performance properties, such as adhesion to the substrate.

By use of preferred inventive mononoble metal dithiolates it is possible to produce aqueous noble metal preparations which are essentially free of organic solvents. Such preparations are characterized in that they contain water as solvent and less than 2 wt. %, relative to the preparation, of organic solvents, a water-soluble polymeric organic binder, a mononoble metal dithiolate, which has at least one functional group capable of salt formation, in the form of an aqueous-soluble salt and in addition an effective amount of a surfactant. The preparations particularly preferably contain a salt prepared from a mono-noble metal dithiolate having one or more carboxyl groups and a primary, secondary or tertiary amine or an N-heterocyclic base. The proportion of organic solvents is preferably less than 1 wt. %, especially 0 wt. %, relative to the preparation. The stated residual content of organic solvents may arise from the use of the auxiliary substances used, if these are commercially available in the form of organic solutions, and are used in this form.

The mononoble metal dithiolates which may be used in the aqueous-organic and purely aqueous preparations according to the invention have structural components, namely at least one acidic or basic group capable of salt formation, which impart sufficient water-solubility to them. The preparations generally contain from 2 to 25 wt. %, preferably 5 to 15 wt. %, of noble metal in the form of one or more thiolates. The water-solubility of the thiolates must accordingly be higher at an elevated noble metal content than at a lower content. It is always intended to achieve a high-quality decoration at lowest demand of gold.

Water-based preparations according to the invention contain polymeric binders which are soluble in water or which form a clear dispersion in water. Useful binders are polyacrylic acid, polymethacrylic acid, polyvinyl pyrrolidone, cellulose ethers, more particularly carboxyalkyl and hydroxyalkyl cellulose, polyalkylene glycol, polyvinyl acetate, polyvinyl alcohol, polyamines, alkyd resins and polyurethane resins. The binders may be used in the form of homopolymers or copolymers or block polymers either individually or in the form of mixtures. Polyvinyl pyrrolidone homopolymers or copolymers, polymethacrylic acid homopolymers or copolymers and resins based on cellulose ethers are particularly preferred for essentially purely aqueous preparations and preparations having a high water content.

The proportion of polymeric binders in the aqueous-organic and purely aqueous preparations is customarily in the range between 3 and 45 wt. %, preferably between 3 and 20 wt. % and in particular 4 to 10 wt. %. The weight ratio of binder to noble metal in the preparations is conveniently in the range between 0.1 and 2, preferably between 0.3 and 1.2 and in particular between 0.5 and 1.0.

The water content of aqueous-organic preparations is generally between 10 and 80% by weight and preferably between 30 and 60% by weight while the organic solvent content is between 10 and 40% by weight, based on the preparation.

The water content of essentially purely aqueous preparations is generally between 10 and 90 wt. %, preferably between 40 and 80 wt. %, in each case relative to the preparation.

Preparations containing an aqueous/organic solvent system contain one or more water-soluble organic solvents, more particularly water-soluble alcohols, ethers and esters, as the organic solvent. Glycols containing 2 to 4 carbon atoms and oligo- and poly-($C_{2-4}$)-glycols or mono($C_{1-4}$) alkyl ethers of the above-mentioned glycols or oligoglycols, ($C_{2-5}$) hydroxycarboxylic acids or lower alkyl esters thereof, such as in particular $C_{1-3}$ alkyl lactate, are particularly preferred.

A constituent of the essentially purely aqueous preparations which is essential to the invention is an effective quantity of a surfactant compatible with the thiolate salt selected from the range of anionic, non-ionic, zwitterionic and cationic surfactants. The person skilled in the art will verify the compatibility and efficacy of a selected surfactant by means of investigatory tests, as interactions with the other constituents of the preparations may also occur. A good effect is customarily achieved with a quantity of surfactant of between 0.1 and 2 wt. %, relative to the preparation; larger or smaller quantities are, however, also possible in individual cases. The surfactant content is preferably between 0.2 and 1 wt. %.

Each molecule of the surfactants contains a hydrophobic residue with 8 to 26 and in particular 10 to 18 C atoms or another hydrophobic group, such as, for example, a group based in polydimethylsiloxane, and at least one anionic, zwitterionic, non-ionic or cationic water solubilising group.

Examples of suitable anionic surfactants which may be cited are: straight-chain or branched alkylbenzene sulphonates, in particular those with a straight-chain $C_8$ to $C_{16}$ alkyl group, aliphatic and olefinic ($C_8$ to $C_{18}$) sulphonates, hydroxyalkane sulphonates, fatty acid esters of oxyethanesulphonic acid; fatty alcohol sulphates, sulphated fatty acid alkylolamides and fatty acid monoglycerides together with sulphated alkoxylation products of fatty alcohols, alkylphenols, fatty acid amides; saturated and unsaturated fatty acid salts, alkyl and alkenyl ether carboxylic acid salts containing a ($C_{10}$ to $C_{20}$) alkyl or alkenyl group and a polyethylene glycol group comprising 1 to 8 units; α-sulpho fatty acids; amide-type condensation products of fatty acids or sulphonic acids with aminocarboxylic acids, such as glycine, sarcosine, protein hydrolysates. Particularly suitable anionic surfactants are alkylbenzene sulphonates with 8 to 14 C atoms, in particular in the form of a salt with an amine in a quantity of 0.1 to 2 wt. %, preferably 0.2 to 1 wt. %, relative to the preparation.

Non-ionic surfactants owe their water-solubility to the presence of polyether groups, as well as amine oxide, sulphoxide, phosphine oxide and alkylolamide groups. Alkoxylation products are of particular interest, especially ethoxylation products of fatty alcohols, alkylphenols, fatty amines, alkanolamines, fatty acids, fatty acid amides and sulphonic acid amides.

Another group of non-ionic surfactants which are particularly effective in the essentially purely aqueous preparations according to the invention are water-soluble polyether-modified polysiloxanes—these are polyether-polysiloxane copolymers, wherein linear or branched block copolymer structures may be present. The quantity used of this class is preferably between 0.1 and 2.0 wt. %, in particular between 0.2 and 1.0 wt. %, relative to the preparation. The polyether segments are polyoxyethylene, polyoxypropylene or poly (oxyethylene-oxypropylene) segments, wherein polyoxyethylene segments and in particular those with 4 to 20 oxyethylene units are preferred. The polysiloxane segments are preferably based on dimethylsiloxane. The polyether and polysiloxane segments may be attached to each other by Si—O—C— or Si—C— bonds. Reference is, for example, made to Ullmann's Encyclopedia of Industrial Chemistry, 5th edition, volume A 24, p. 83–84 (1993) and Ind. Eng. Chem. Proc. Res., Dev. 6 (1967), p. 88–92.

Zwitterionic surfactants contain both an acidic group, such as a carboxyl, sulphonic acid, sulphuric acid semiester or phosphoric acid partial ester group, and a basic hydrophilic group, such as a primary, secondary, tertiary, quaternary ammonium group. Such surfactants include betaines, such as those of the type

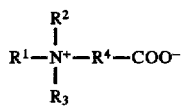

where $R^1$ is alkyl, alkenyl, hydroxyalkyl with 8 to 24 C atoms, $R^2$ and $R^3$ are identical or different alkyl or hydroxyalkyl with 1 to 4 C atoms, $R^4$ is alkylene or hydroxyalkylene with 1 to 6 C atoms.

The cationic surfactants are mainly substances of the formula

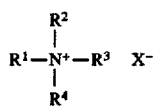

where $R^1$ is alkyl or alkenyl with 8 to 24 C atoms, $R^2$ to $R^4$ are alkyl or hydroxyalkyl with 1 to 5 C atoms and $X^-$ is a halogen atom.

For influencing color, gilding preparations, more particularly bright gold and burnished gold preparations, contain a small quantity of one or more other noble metal compounds substantially soluble in the system in the form of resinates or sulforesinates or in the form of simple noble salts or complexes. In addition, the preparations typically contain fluxes in the form of compounds, for example resinates, salts, oxides or coordination compounds of one or more of the elements boron, silicon, vanadium, chromium, indium, tin, antimony, bismuth and rhodium. The quantity of flux used is typically between 0.01 and 2% by weight, based on the preparation.

Other auxiliaries in the preparations according to the invention may be typical substances for varying the rheological properties of the preparation, surfactants, adhesion-strengthening auxiliaries and also drying accelerators where a UV-curable resin is used. The additional use of an aqueous polysulfide solution has proved to be useful in some cases, particularly in preparations containing polyvinyl pyrrolidone. In general, so-called burnished gold preparations additionally contain gold powder and/or fine-particle insoluble gold compounds. Depending on the required effect, burnished gold preparations may additionally contain glass frits and/or organosilicon compounds.

On production of the aqueous preparations, a water-soluble salt of a mononoble metal dithiolate is used directly or the salt is formed in situ in water at room temperature or elevated temperature, preferably at 30° to 80° C., from at least one mononoble metal dithiolate having at least one acidic functional group and base, such as an alkali metal hydroxide solution, ammonia or an amine, or from a mononoble metal dithiolate having an amino group and an acid, such as a lower carboxylic acid.

The quantity of base used for each mol of thiolate is generally the quantity necessary to neutralise the acid groups; complete solution is sometimes achieved even with a deficit of base. An excess of base is possible, but not generally necessary. The fluxes are added to the resultant solution and dissolved. The binder is then directly added to the solution and dissolved therein. Alternatively, the binder or binder mixture, optionally with the addition of further auxiliary substances, such as for example a polysulphide solution, may be dissolved in water and this solution combined with the solution containing noble metal. The surfactant is added to one of the solutions during production of the preparation or to the preparation itself on completion of production.

The preparations according to the invention containing mononoble metal dithiolates may be directly applied to the surface to be decorated by conventional decoration processes, such as spraying, brushing or known printing processes, more particularly screen printing processes, and the decoration can be fired at a temperature of generally 400° to 900° C. after evaporation of the solvent components. Alternatively, the noble metal preparation according to the invention may be applied to the substrate to be decorated using a transfer. The transfer is produced in known manner, the monogold(I) dithiolate compound according to the invention being present in the decorative layer of the transfer. A decorative layer is applied to a water-soluble separation layer disposed on a support or a thermo-separation layer using a noblemetal-containing preparation of the type described in the foregoing, after which the solvent components are allowed to evaporate and the binder is optionally crosslinked; a film is normally applied to the decoration layer.

The invention provides a new class of compounds which are eminently suitable for the production of film-like noble-metal-containing decorations. The decorations are surprisingly glossy and adhere excellently to the substrate because a coherent film is formed. The mono-noble metal dithiolates according to the invention provide the expert with a new class of compounds which may be used not only in conventional noble metal preparations essentially containing only organic solvents as their solvent component, but also in noble metal preparations which contain an aqueous/organic solvent system or even essentially water as the only solvent. The production of new noble metal compounds and their eminent suitability in water-containing preparations for the decoration of firing-resistant substrates are described in the Examples. The Comparison Examples show that satisfactory noble metal decorations cannot be produced with structurally similar compounds in which there is no second mercapto group.

The decoration produced by use of preparations in accordance with the invention is of surprisingly elevated brightness and adheres excellently to the substrate surface as a continuous film is formed. It is additionally possible to produce spot- and pore-free films which fulfil aesthetic requirements.

With regard to the prior art, it was not predictable that it would be possible to provide noble metal preparations for the production of noble metal decoration, in particular bright gold decoration, in which it is possible to dispense with the use of organic solvents. It is possible, as is shown by the following examples, by means of the combination according to the invention of specific thiolates, water-soluble polymers and a surfactant, to obtain purely aqueous preparations and to use them to produce high-quality decoration on stovable substrates.

EXAMPLE 1

Preparation of Monogold Dimercaptosuccinic Acid a) 0.035 mole=18.49 g of $HAuCl_4$ (37.29% Au) is added dropwise with stirring to a suspension of 0.07 mole of methionine in 70 ml of $H_2O$. The temperature is kept at 0° to 5° C. by external cooling. On completion of the reaction, the gold(I) complex is added dropwise over a period of 1 hour to a suspension of 0.035 mole=6.38 g of meso-2,3-dimercaptosuccinic acid in 150 ml of dichloromethane. The precipitate is filtered of under suction, washed repeatedly with water and dried in vacuo over blue gel in an exsiccator. The yield of monogold dimercaptosuccinic acid comprises 96.5%, based on the gold used.

| Analysis: | Au | C | H | S |
|---|---|---|---|---|
| Calculated: | 52.09% | 12.70% | 1.33% | 16.96% |
| Found: | 50.81% | 12.05% | 1.52% | 15.62% |
| Begin of decomposition: 194° C. | | | | |

$^{13}$C-NMR in $D_2O$+trimethylamine δ/ppm 52.58 (CH), 60.95 (CH), 180.64 ($CO_2^-$) and 182.51 ($CO_2^-$).

b) Example 1a was repeated using water instead of dichloromethane. In this case, too, highly pure monogold(I) dimercaptosuccinic acid was obtained in a high yield.

Comparison Example 1

The following constituents are mixed in the same way as in Comparison Example 7 of EP-A 0 514 073:

| | Parts by weight |
|---|---|
| Polymethacrylate resin (Versicol K11 of Allied Colloids) | 11 |
| Gold mercaptosuccinic acid | 18 |
| Propane-1,3-diol | 15 |
| Water | 40 |
| Isopropanol | 15 |
| Rhodium complex | 0.04 |
| Chromium trioxide | 0.05 |

The preparation is brushed onto porcelain and heated for 10 minutes at 820° C., the heating-up time being 1 hour. A matt film is obtained. Gloss measurements produced the following results:

| Angle | Gloss units | Standard deviation |
|---|---|---|
| 20° | 58.3 | 5.4 |
| 60° | 54.2 | 4.1 |

The gloss measurements were carried out with a ByK Gardner "haze-gloss" reflectometer. The preparation was brushed onto a 4 cm×4 cm porcelain plate and measured at various places. The results are expressed as the mean value of the individual measurements, the associated standard deviation as indicated by the measuring instrument and the angle at which the measurements were carried out.

Comparison Example 2

The following composition is prepared in the same way as in Comparison Example 1:

| | Parts by weight |
|---|---|
| Polyvinyl pyrrolidone (PVP K25, a product of Fluka) | 8.1 |
| Gold mercaptosuccinic acid | 17.2 |
| Propane-1,2-diol | 8.1 |
| Water | 39.9 |
| Ethyl lactate | 16.2 |
| Rhodium complex | 0.15 |
| Chromium sulfate | 0.04 |
| Ammonium bismuth citrate | 0.44 |
| Triethylamine | 5.3 |
| Ammonium polysulfide solution (15% in water) | 1.9 |
| Silver mercaptopropionyl glycine | 2.6 |

The preparation is brushed onto porcelain and heated for 10 minutes at 820° C., the heating-up time being 1 hour. A matt film is obtained. Gloss measurements produced the following results:

| Angle | Gloss units | Standard deviation |
|---|---|---|
| 20° | 20.1 | 4.6 |
| 60° | 38.2 | 2.1 |

EXAMPLE 2

In contrast to Comparison Example 2, the gold compound of Example 1 according to the invention was used in otherwise the same composition:

| | Parts by weight |
|---|---|
| PVP K25 | 8.1 |
| Monogold dimercaptosuccinic acid | 18.8 |
| Propane-1,2-diol | 8.1 |
| Water | 38.3 |
| Ethyl lactate | 16.2 |
| Rhodium complex | 0.15 |
| Chromium sulfate | 0.04 |
| Ammonium bismuth citrate | 0.44 |
| Triethylamine | 5.3 |
| Ammonium polysulfide solution (15%) | 1.9 |
| Silver mercaptopropionyl glycine | 2.6 |

The preparation is brushed onto porcelain and heated for 10 minutes at 820° C., the heating-up time being 1 hour. A glossy, firmly adhering film is obtained. Gloss measurements produced the following results:

| Angle | Gloss units | Standard deviation |
|---|---|---|
| 20° | 741 | 42.4 |
| 60° | 503 | 6.4 |

EXAMPLE 3

The following constituents were mixed:

| | Parts by weight |
|---|---|
| PVP K25 | 8.6 |
| Monogoid dimercaptosuccinic acid | 19.5 |
| Propane-1,2-diol | 8.6 |
| Water | 34.3 |
| Ethyl lactate | 17.3 |
| Rhodium complex | 0.16 |
| Chromium sulfate | 0.07 |
| Ammonium bismuth citrate | 0.53 |
| Triethylamine | 5.7 |
| Ammonium polysulfide solution (15%) | 2.6 |
| Monosilver dimercapto succinic acid | 2.6 |

The preparation was brushed onto porcelain and heated for 2 minutes at 880° C., the heating-up time being 30 minutes. A glossy, firmly adhering film is obtained.

EXAMPLES 4 TO 8

Using the procedure described in Example 1, other monogold dimercapto compounds were prepared by reaction of the gold(I) methionine complex with other dimercapto compounds in a molar ratio of 1:1:

Example 4: Reaction with 1,4-dimercaptobutane-2,3-diol: the Au content of the isolated product was 67.01% (theor. 56.24).

Example 5: Reaction with 2,3-dimercapto-1-propane sulfonic acid sodium salt: Au content 57.45% (theor. 46.43%). The product obtained, which consisted essentially of the monogold compound and partly—it would appear—of the digold compound of the sulfonic acid mentioned, dissolved smoothly in water. The product is suitable for the production of noble metal decorations, particularly those which give a silk-like sheen after polishing.

Example 6: Reaction with 6,8-dimercaptooctanoic acid: Au content 57.47% (theor. 48.72%). The compound is suitable as a gold preparation in organic decorative preparations, but not in aqueous preparations on account of its poor solubility in water.

Example 7: Reaction with N-(3'-mercapto-2'-methylpropionyl)-2-amino-4-mercaptobutanoic acid: Au content 51.22% (theor. 45.46%). The monogold dimercapto compound obtained is suitable as an Au compound in organic and aqueous decorative preparations which fire elegantly and produce a glossy and light decoration.

Example 8: Reaction with α,α'-dimercaptoadipic acid: Au content 49.07% (theor. 48.48%). In decorative preparations, the Au compound is slightly dull after firing, but produces a very attractive light gloss after gentle polishing. Accordingly, the Au compound is particularly suitable in burnished gold preparations with a low percentage Au content. The low gold content is an advantage compared to usual burnish gold preparations.

EXAMPLE 9

Bright Gold Preparation

An aqueous solution containing monogold(I) dimercaptosuccinic acid was prepared in accordance with a general work instruction. Triethylamine was used as the base. Rhodium chloride, chromium sulphate and ammonium bismuth citrate were then added as fluxes. An aqueous polyvinyl-pyrrolidone solution, which additionally contained ammonium polysulphide, was added to the resultant solution, together with a polyether-modified polydimethylsiloxane (ByK®346) as the surfactant. The preparation contained only approximately 0.5 wt. % of an organic solvent contained in the customary commercial surfactant solution and was otherwise purely aqueous.

The noble metal and flux contents, calculated as stated, and the content of binder, surfactant and auxiliary substances in the preparation may be found in the table.

| Constituents | wt. % in preparation |
|---|---|
| Au content | 9.35 |
| Rh content | 0.06 |
| $Cr_2O_3$ content | 0.13 |
| $Bi_2O_3$ | 0.21 |
| Polyvinylpyrrolidone (PVP K25 from Fluka) | 5.2 |
| Surfactant solution (ByK ® 346); surfactant content 46%) | 1.0 |
| $N(C_2H_5)_3$ (for salt formation) | 4.8 |
| $(NH_4)_2 Sx$ | 0.15 |

EXAMPLES 10 AND 11

Substantially purely aqueous bright gold preparations were produced in a similar manner to example 9, wherein the product from example 1 was used as the Au thiolate and silver 2-mercaptopropionylglycine was additionally used as the silver thiolate. The binder used was a hydroxyethyl cellulose (Natrasol from Aqualon Ltd., UK); a polysulphide was not used. ByK®346 was again used as the surfactant in the preparation according to the invention of example 10; the preparation of example 11, which was not according to the invention, contained no surfactant. The contents of the constituents may be found in the table.

| | Example 10 | Example 11 |
|---|---|---|
| | (wt. % in preparation, calculated as stated) | |
| Au content | 9.62 | 9.71 |
| Ag content | 1.08 | 1.10 |
| Rh content | 0.07 | 0.07 |
| $Cr_2O_3$ content | 0.01 | 0.01 |
| $Bi_2O_3$ content | 0.30 | 0.30 |
| Hydroxyethyl cellulose | 5.3 | 5.3 |
| Surfactant solution (ByK ® 346; surfactant content 46%) | 1.0 | — |
| $N(C_2H_5)_3$ (for salt formation) | 5.3 | 5.3 |

EXAMPLE 12

Decoration of Porcelain

Application of preparations of examples 9, 10 and 11 by screen printing (examples 12/9, 12/10, 12/11).

Firing conditions: heating to 820° C. in 1 h, holding time at 820° C. 10 minutes.

Bright and spot-free decorative films with good adhesion were obtained using the preparations according to the invention of examples 9 and 10. Only spotty decoration was obtained using the surfactant-free preparation of example 11, which was not according to the invention.

We claim:

1. A mononoble metal dithiolate of the formula (A):

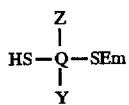

in which
Em is a noble metal selected from the group consisting of Au(I), Ag(I), Pd(II), Pt(II) and Rh(III), Q is a tetravalent organic radical containing 2 to 10 carbon atoms, Y is a hydrophilic group selected from the group consisting of (1) —COOH, (2) —COO⁻cat⁺, where cat⁺ is Li⁺, Na⁺, K⁺, NH₄⁺, $(C_{1-3}alkyl)_n N^+H_{(4-n)}$ or $(hydroxy-(C_{1-3})-alkyl)_n N^+H_{(4-n)}$ and n is an integer of 1 to 4, and (3)

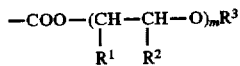

where $R^1$, $R^2$ and $R^3$ may be the same or different and represent H or methyl and m is an integer of 1 to 12, Z has the same meaning as Y or represents —H or a member selected from the group consisting of —OR', —SR', —SO₃R', —NR'₂, NR'₃⁺X⁻, where X⁻ is a mineral acid or carboxylic acid anion and R' is hydrogen or the group

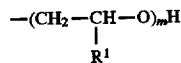

wherein
$R^1$ is H or methyl and
m is an integer of 1 to 12.

2. A mononoble metal dithiolate as claimed in claim 1, wherein Em stands for gold or silver in the oxidation stage (I).

3. A mononoble metal dithiolate as claimed in claim 1 or 2, which is soluble in water and wherein at least one of Y and Z represents COO⁻cat⁺ or wherein Y is a carboxyl group and Z is an amino group of the formula —NR'₂ capable of forming an inner salt with the carboxyl group and wherein cat⁺ and R' are as defined in claim 1.

4. A mononoble metal dithiolate as claimed in claim 1 or 2, wherein the organic radical Q is an aliphatic $C_{2-4}$ alkane tetrayl radical or a 5- or 6-membered cycloaliphatic tetrayl radical optionally containing an oxygen or imine ring member.

5. A mononoble metal dithiolate as claimed in claim 3, wherein the organic radical Q is an aliphatic $C_{2-4}$ alkane tetrayl radical or a 5- or 6-membered cycloaliphatic tetrayl radical optionally containing an oxygen or imine ring member.

6. A mononoble metal dithiolate as claimed in claim 1 or 2, which is monogold(I) or monosilver dimercaptosuccinic acid or a salt thereof.

7. A mononoble metal dithiolate as claimed in claim 3, which is monogold(I) or monosilver dimercaptosuccinic acid or a salt thereof.

8. A mononoble metal dithiolate as claimed in claim 4, which is monogold(I) or monosilver dimercaptosuccinic acid or a salt thereof.

9. A process for the production of a mononoble metal dithiolate of the formula (A'):

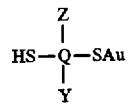

in which Q, Z and Y are as defined in claim 1, which comprises reacting an Au(I) complex of the formula AuCl.R"SR'", where R"S'" is a thioether, with a substantially equivalent molar quantity of a thiol in the presence of a solvent, the thiol used being a thiol of the formula (B):

in which Q, Y and Z are as defined in claim 1.

10. A process as defined in claim 9, wherein the thioether R"S'" is methionine.

11. A process for the production of a mono-noble metal dithiolate of formula A of claim 1, wherein Em represents Ag(I), Pd(II) or Pt(II) which comprises reacting a soluble salt of Ag(I), Pd(II) or Pt(II) with a thiol compound, of the formula B

wherein Q, Y and Z are as defined in claim 1.

12. In a noblemetal-containing preparation for decorating a firing-resistant substrate, to produce a noble metal decoration, said preparation containing at least one noble metal thiolate, at least one polymeric organic binder, at least one solvent for the noble metal thiolate, at least one binder and, optionally, at least one auxiliary for adjusting the processing properties of the preparation and the optical and performance properties of the noblemetal-containing decoration to be produced therewith, the improvement wherein the preparation contains at least one mononoble metal dithiolate as defined in claim 1 as the noble metal thiolate.

13. A preparation as claimed in claim 12, wherein in the mononoble metal dithiolate Em stands for gold or silver in the oxidation stage (I).

14. A preparation as defined in claim 12, wherein the firing-resistant substrate is glass.

15. A preparation as claimed in claim 12, containing a polar organic solvent and water as the solvent component.

16. A preparation as defined in claim 15, wherein the polar organic solvent is selected from the group consisting of (1) $C_{2-4}$ glycols or $C_{1-4}$ monoethers thereof, (2) oligo($C_{2-4}$) glycols or $C_{1-4}$ monoethers thereof, and (3) ($C_{2-3}$) hydroxycarboxylic acids and ($C_{1-3}$) alkyl esters thereof.

17. A preparation as claimed in claim 12, containing water as solvent and less than 2 wt. %, relative to the preparation, of organic solvent, a mono-noble metal dithiolate as defined in claim 1, which has at least one functional group capable of salt formation, in the form of an aqueous salt, a water-soluble polymeric organic binder and an effective quantity of a surfactant.

18. A preparation according to claim 12, wherein the polymeric organic binder is selected from the group consisting of polyvinylpyrrolidone homo- or copolymers, polyacrylic acid homo- or copolymers, polymethacrylic acid homo- or copolymers, water-soluble cellulose ethers, and mixtures thereof.

19. A preparation according to claim 12, containing a salt prepared from a mono-noble metal dithiolate containing at least one carboxyl group, and a primary, secondary or tertiary amine or an N-heterocyclic base.

20. A preparation according to claim 12, wherein the mono-noble metal dithiolate is present in the form of a salt with tri($C_1$ to $C_3$)alkylamine or mono-, di- or triethanolamine and the preparation additionally contains at least one auxiliary substance to adjust the optical and service properties of the decoration to be produced and/or the processing characteristics of the preparation.

21. A preparation according to claim 20, containing a salt of monogold(I) dimercaptosuccinic acid.

22. A preparation according to claim 17, containing as surfactant 0.1 to 2.0 wt. %, of a polyoxyethylene-polydimethylsiloxane.

23. A preparation according to claim 22, wherein the amount of the surfactant is 0.2 to 1.0 wt. %.

24. A preparation according to claim 17, wherein the surfactant is an alkylbenzene sulphonate with 8 to 14 C atoms in the alkyl group in the form of a salt with an amine in a quantity of 0.1 to 2 wt. %.

25. A preparation according to claim 24, wherein the amount of the surfactant is 0.2 to 1.0 wt. %.

26. In a transfer for producing noble-metal-containing decorations on firing-resistant substrates, said transfer containing in a decoration layer one or more noble metal thiolates and one or more polymeric organic binders and, optionally, at least one auxiliary from the production of the transfer and for influencing the optical properties and performance properties of the noble-metal-containing decoration to be produced, the improvement wherein a mononoble metal dithiolate as defined in claim 1 is present in uniform distribution as the noble metal thiolate in the decoration layer.

27. In a process for decorating a stovable substrate by applying a preparation containing a noble metal thiolate or a transfer containing this preparation in a dry state onto the substrate and stoving at 400° to 900° C., the improvement wherein a preparation according to claim 12 or a transfer containing this preparation is used.

28. A process according to claim 27, wherein the stovable substrate is glass.

* * * * *